(12) United States Patent
Azuma et al.

(10) Patent No.: US 8,132,462 B2
(45) Date of Patent: Mar. 13, 2012

(54) ULTRASONOGRAPHIC DEVICE

(75) Inventors: Takashi Azuma, Kodaira (JP);
Shinichiro Umemura, Sendai (JP);
Tatsuya Nagata, Ishioka (JP); Hiroshi Fukuda, London (GB); Shuntaro Machida, Kokubunji (JP); Toshiyuki Mine, Fussa (JP)

(73) Assignee: Hitachi Medical Corporation, Tokyo (JP)

( * ) Notice: Subject to any disclaimer, the term of this patent is extended or adjusted under 35 U.S.C. 154(b) by 694 days.

(21) Appl. No.: 11/996,532

(22) PCT Filed: Jan. 30, 2006

(86) PCT No.: PCT/JP2006/301403
§ 371 (c)(1),
(2), (4) Date: Feb. 19, 2009

(87) PCT Pub. No.: WO2007/029357
PCT Pub. Date: Mar. 15, 2007

(65) Prior Publication Data
US 2009/0301199 A1      Dec. 10, 2009

(30) Foreign Application Priority Data

Sep. 5, 2005   (JP) ................................ 2005-255821

(51) Int. Cl.
*G01N 29/34*       (2006.01)
*H02N 1/08*        (2006.01)
(52) U.S. Cl. .............................. 73/603; 73/596; 310/300
(58) Field of Classification Search .................... 73/603; 600/443, 459; 310/309, 306, 311, 334
See application file for complete search history.

(56) References Cited

U.S. PATENT DOCUMENTS 5,664,456 A * 9/1997 Eckert .......................... 73/290 V
6,056,693 A * 5/2000 Haider .......................... 600/443
(Continued)

FOREIGN PATENT DOCUMENTS

CN           1553785         12/2004
(Continued)

OTHER PUBLICATIONS

Johnson et al, "Medical Imaging Using Capacitive Micromachined Ultrasonic Transducer Arrays" Ultrasonics, IPC Science and Technology Press Ltd, Guilford, GB LNKD-DOI: 10:1016/S0041-624X(02) 00161-0, vol. 40, No. 1-8, May 1, 2002; pp. 471-476.

(Continued)

*Primary Examiner* — J M Saint Surin
(74) *Attorney, Agent, or Firm* — Antonelli, Terry, Stout & Kraus, LLP.

(57) ABSTRACT

The receive sensitivity of an ultrasound array transducer structured with a diaphragm electro-acoustic transducer (101) being a basic unit is affected by change in a charge amount with elapsed time due to leakage or the like, which causes drift of the primary beam sensitivity, degradation in the acoustic SN ratio due to a rise in the acoustic noise level, and degradation in the directivity of an ultrasound beam. To addressing this problem, a charge controller (charge monitor 211) is provided to control charge in an electro-acoustic transducer (101). A charge monitoring section (102) monitors the change in the charge amount. When change in the charge amount is small, transmit sensitivity or receive sensitivity is calibrated by a controller (104) by, for example, multiplying a receive signal by a calibration coefficient corresponding to the change amount. Further, when the change in the charge amount is large, for example, charges can be re-emitted from a charge emitter (103).

16 Claims, 11 Drawing Sheets

U.S. PATENT DOCUMENTS

| | | | |
|---|---|---|---|
| 6,359,367 B1 | 3/2002 | Sumanaweera | |
| 6,443,901 B1 | 9/2002 | Fraser | |
| 7,612,485 B2 * | 11/2009 | Sugiura et al. | 310/324 |
| 7,775,110 B2 * | 8/2010 | Okuda et al. | 73/627 |
| 7,877,854 B2 * | 2/2011 | Sliwa et al. | 29/594 |
| 2009/0299192 A1 * | 12/2009 | Asafusa et al. | 600/459 |
| 2009/0301200 A1 * | 12/2009 | Tanaka et al. | 73/603 |
| 2010/0137719 A1 * | 6/2010 | Ikeda et al. | 600/459 |

FOREIGN PATENT DOCUMENTS

| | | |
|---|---|---|
| JP | 07-311231 | 11/1995 |
| JP | 2004-503313 | 2/2004 |
| WO | WO 01/97562 | 12/2001 |
| WO | WO 01/97562 A2 | 12/2001 |
| WO | PCT/JP02/09115 | 9/2002 |

OTHER PUBLICATIONS

Oralkan Omer et al; "Capacitive micromachined ultrasonic transducer: next-generation arrays for acoustic imaging"; IEEE Transactions on Ultrasonics, Ferroelectrics, And Frequency Control Nov. 2002, LNKD-PUBMED: 12484483, vol. 49, No. 11, Nov. 2002 pp. 1596-1610.

IEEE 1994 Ultrasonics Symposium, pp. 1241-1244, Haller et al, A surface micromachined Electrostatic Ultrasonic Air Transducer.

J. Acoust. Soc. Am. 75(4), Apr. 1984, pp. 1297-1298, Silicon-dioxide Electret Transducer, Hohm et al.

IEEE Transactions on Dielectrics and Electrical Insulation vol. 3, No. 4, Aug. 1996, pp. 494-498, "Silicon based Inorganic Electrets For Application In Mlcromachined Devices," Amjadi et al.

* cited by examiner lateral direction

ULTRASONOGRAPHIC DEVICE

TECHNICAL FIELD

The present invention relates to a transducer for transmitting/receiving ultrasound, and particularly relates to a silicon-based diaphragm ultrasound transducer.

BACKGROUND ART

Although most ultrasound transducers for practical use are still piezoelectric ceramic ultrasound transducers (PZT), a fine diaphragm transducer has been researched and developed since the 1990's to take the place of the ceramic ultrasound transducer by the use of semiconductor micro-processing technology, such as represented by the technology disclosed on pages 1241-1244 of "Proceedings of 1994 IEEE Ultrasonics Symposium."

Although acoustic impedance is constant as a physical property value unique to a material in the case of a conventional piezoelectric transducer using PZT, pseudo-acoustic impedance of a diaphragm structure reflects not only a material but also a structure. Thus, the diaphragm transducer has a degree of freedom in design suitable for a subject.

Recently, development has progressed, and a diaphragm transducer has caught up with a conventional piezoelectric transducer using PZT, also in terms of transmit/receive sensitivity.

An electret transducer using a semiconductor diaphragm structure is disclosed on pages 1297-1298 of "J. Acoust. Soc. Am. Vol. 75 1984." In this transducer, a silicon compound layer accumulating charge is provided at least one of a position between an electrode on a diaphragm side and a cavity and a position between an electrode on a substrate side and the cavity. As a material of a charge accumulating type insulation layer, a silicon compound, such as a silicon oxide film or a silicon nitride film, or a lamination structure thereof, is adopted, as disclosed in the above pages 1297-1298 of "J. Acoust. Soc. Am. Vol. 75 1984," and pages 494-498 of "IEEE Transactions on Dielectrics and Electrical Insulation Vol. 3 No. 4. 1966". An insulation layer of such a silicon compound is formed by vapor phase epitaxial growth represented by CVD (Chemical Vapor Deposition). However, charges can be trapped not only on a surface of the compound layer but also in the compound layer by controlling the quantity of crystal defects. Thus, insulation layers are used as an electro-acoustic transducer, for which a DC bias voltage is unnecessary, by charging the insulation layer in advance in a high electric field.

However, in reality, the charged state of an insulation film is unstable and charges drift, while the insulation film is used. Thus, there arises a problem that electro-acoustic conversion efficiency drifts, the efficiency being the most basic property as an electro-acoustic transducer.

When the conversion efficiency can hardly be stabilized even in a range of a satisfactory level, a major obstacle occurs with a practical use of insulation layers as transducers. The drift of the conversion efficiency causes a change with elapsed time in the device properties, and more particularly, it has a crucial effect on constructing an array converter employing these types of electro-acoustic transducers. The effect causes not only drift of the sensitivity of the whole electro-acoustic converter, but also a risk that, if the electro-acoustic conversion properties of the transducers constituting an array converter drift unevenly, the acoustic noise level is extremely raised when operation for forming transmit and receive beams is performed by the whole electro-acoustic converter.

Accordingly, particularly in order to construct an array converter using charge accumulating type diaphragm electro-acoustic transducers and raise the properties to a practical level, overcoming the problem of drifting is a second significant issue along with the first significant issue of obtaining a large electro-acoustic conversion efficiency.

DISCLOSURE OF THE INVENTION

In the present invention, a charge controller is provided, and a charge amount in each electro-acoustic transducer is controlled. When change in the charge amount is small, transmit sensitivity and/or receive sensitivity is calibrated by the controller by, for example, multiplying a receive signal by a calibration coefficient corresponding to the change amount. Further, when the change in the charge amount is large, for example, charges can be re-emitted from a charge emitter. The series of operations is controlled by the controller, and thus sensitivity variation caused by difference in the changes with elapsed time, and particularly in the changes with elapsed time between the plural transducers, is calibrated.

According to the present invention, drift of transducer properties being a main cause of variation in transducer sensitivities can be suppressed more compared with conventional transducers. Further, in an aspect of the present invention, there is provided an ultrasonographic device capable of suppressing deterioration in a transmit/receive ultrasound beam and preventing a lateral resolution of an image and a dynamic range from dropping.

BEST MODE FOR CARRYING OUT THE INVENTION

Embodiments of the present invention will be described below in detail with reference to the accompanying drawings.

Figure 1:
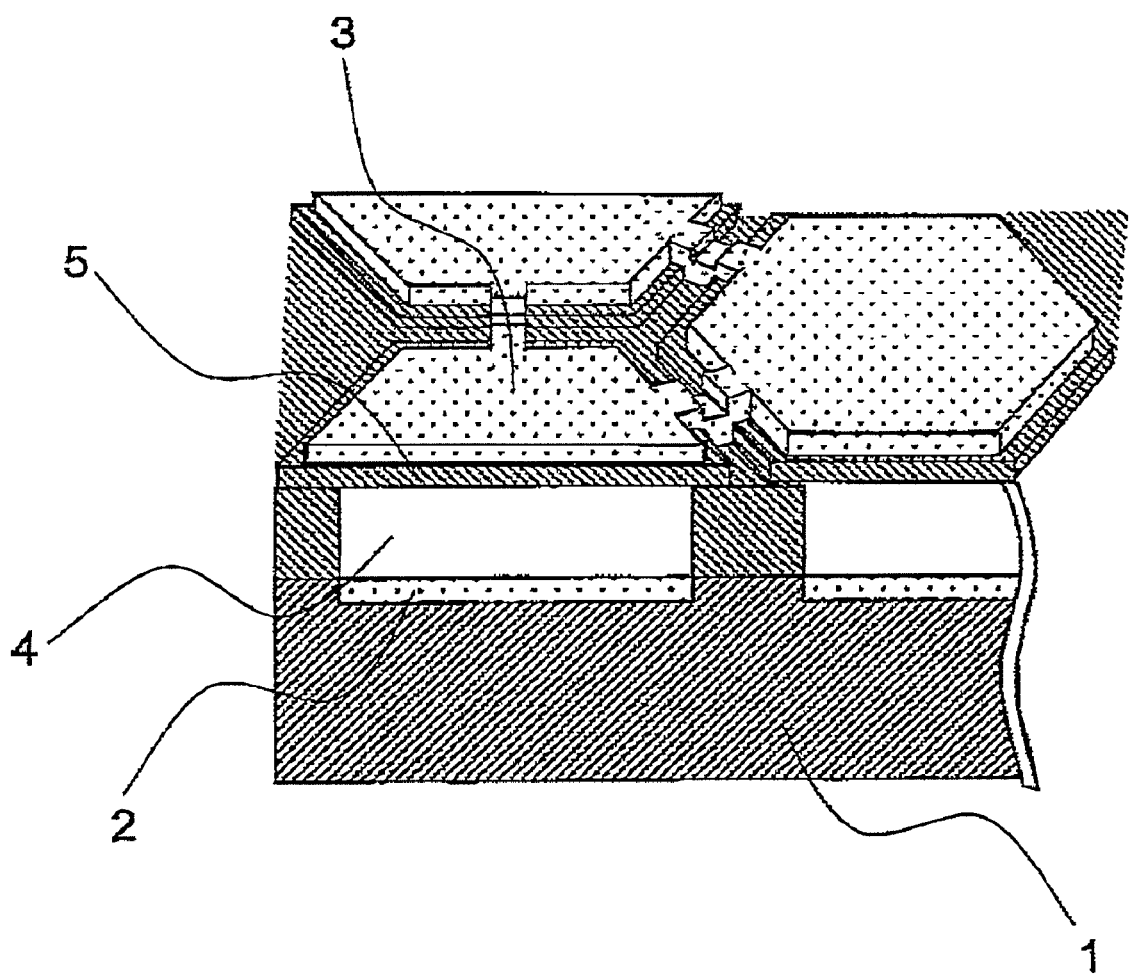
FIG. 1 is a conceptual view of a semiconductor diaphragm electro-acoustic transducer.

In a typical basic structure of an ultrasound transducer using diaphragm electro-acoustic transducers, as shown in FIG. 1, a bottom electrode 2 and a top electrode 3 form a capacitor, the electrodes 2 and 3 being provided respectively on a substrate 1 and a diaphragm 5, with a cavity 4 therebetween. When a voltage is applied between the electrodes 2 and 3, charges are induced in both the electrodes 2 and 3 respectively with opposite polarities, and attract each other, thus the diaphragm 5 being displaced. If the outside of the diaphragm 5 is in contact with water or an organism at this time, a sound wave is radiated into the medium. This is the principle of electro-mechanical conversion in transmission. On the other hand, if a DC bias voltage is applied to induce a certain amount of charges in the electrodes 2 and 3, and oscillation is forcibly applied to the diaphragm from a medium in contact with the diaphragm 5, thereby displacing the diaphragm 5, then an additional voltage is generated in accordance with the displacement. This principle of mechanical-electro conversion in reception of oscillation is the same as that of a DC bias type capacitor micro-phone adopted as a micro-phone for an audible band. Even being made of a mechanically hard material such as silicon, since it has a diaphragm structure having a cavity on the back side, it has a feature capable of achieving an excellent acoustic impedance matching with a mechanically soft material such as an organism or water.

Figure 2:
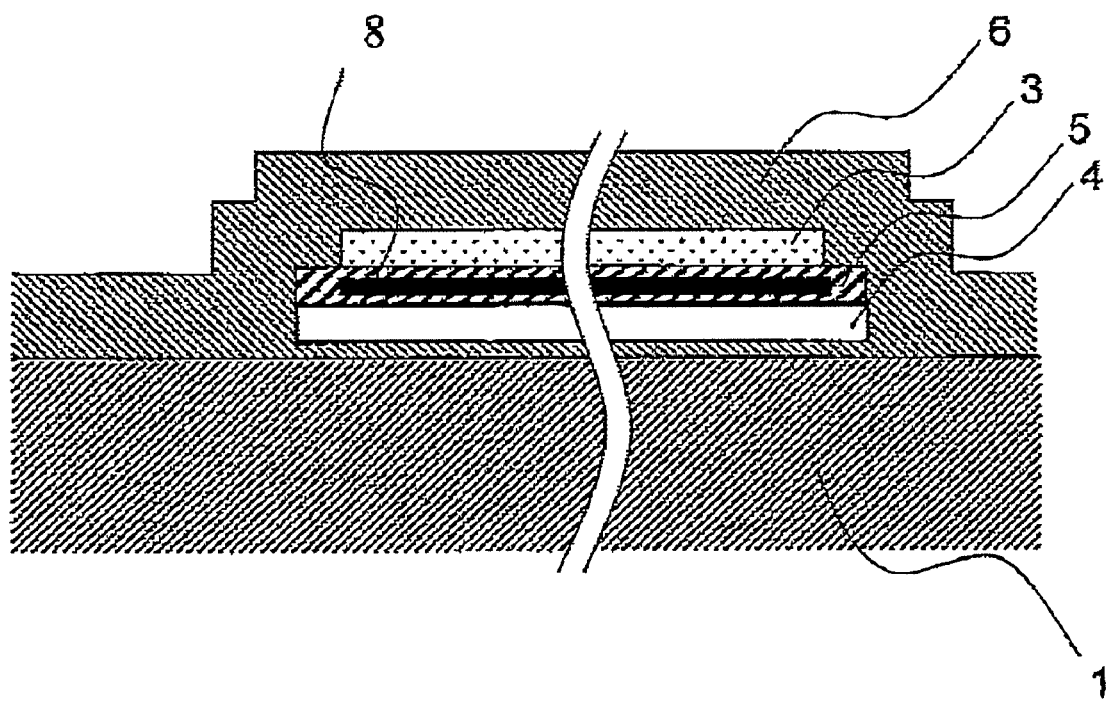
FIG. 2 is a cross sectional view of a silicon-based diaphragm electro-acoustic transducer according to an embodiment of the present invention.
Figure 4:
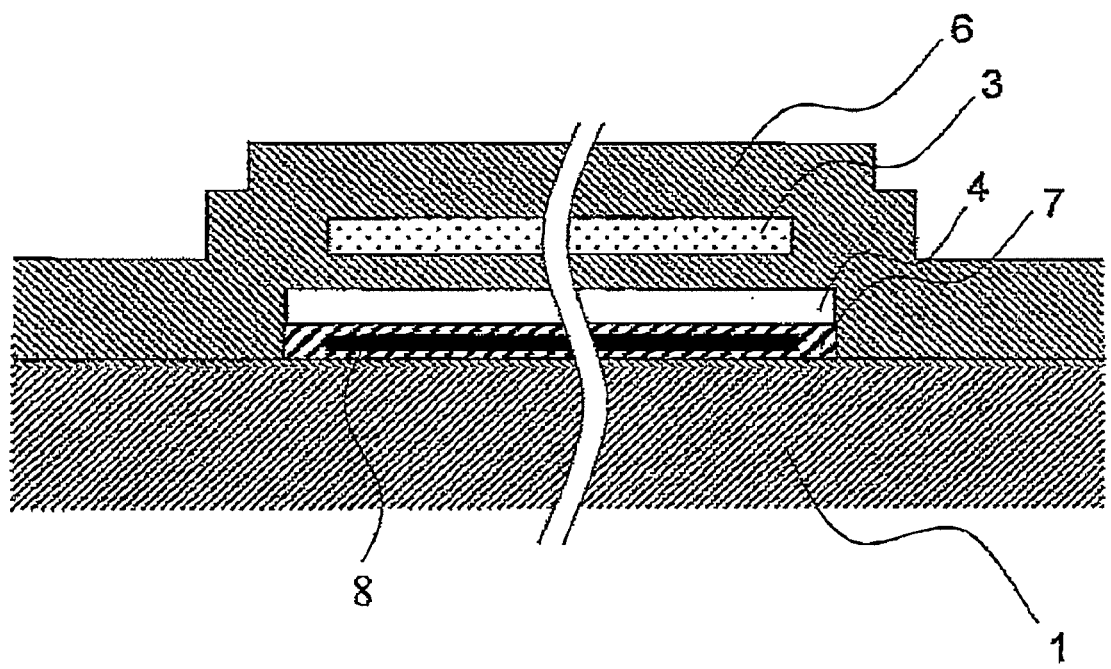
FIG. 4 is a cross sectional view of a silicon-based diaphragm electro-acoustic transducer according to another embodiment of the present invention.

FIG. 2 is a cross sectional view showing a silicon (Si)-based electro-acoustic transducer in an exemplary embodiment of the present invention. An n-type silicon (Si) substrate 1 serving also as a bottom electrode (see the reference symbol 2 in FIG. 1), a first silicon compound layer 6, a cavity layer 4, a second silicon compound layer 5, a top electrode 3 of aluminum, and the silicon compound layer 6 are disposed upward in this order. In the present embodiment, the thicknesses of the first silicon compound layer 6 positioned on the lower side of the cavity, the cavity layer 4, the second silicon compound layer 5, the top electrode 3 and the first silicon compound layer 6 positioned on the top electrode are 30 nm, 100 nm, 200 nm, 200 nm and 1500 nm, respectively, and the inner diameter of the cavity layer 4 positioned on the lower side of the diaphragm is 50 μm. The first silicon compound layer 6 is formed of common silicon nitride $Si_3N_4$, and the mechanical strength of the diaphragm is mainly held by the layer 6 positioned on the top electrode 3. A charge layer 8 having a thickness of 50 nm is implanted in the second silicon compound layer 5. The second silicon compound layer 5 surrounding the charge layer 8 is formed of $SiO_2$ or the like so that generation of a leak current between the charge layer 8 and the electrode is prevented. As shown in FIG. 4, regarding the charge layer 8, the layer between the bottom electrode 1 and the cavity layer 4 may be arranged as a second silicon compound layer 7 to be implanted in the first silicon compound layer 6. To implant the charge layer 8 in this case, the only alterations are that the thickness of the first silicon compound layer 6 is changed from 30 nm (in the example shown in FIG. 2) to 200 nm, the material thereof is changed to that of the second silicon compound, the thickness of the second silicon compound layer 5 is changed from 200 nm to approximately 50 nm (as thin as possible within a range of produceability) and the material thereof is changed to that of the first silicon compound. An object of the present invention can be achieved regardless of whether the charge layer 8 is disposed above or below the cavity layer 4.

Figure 3:
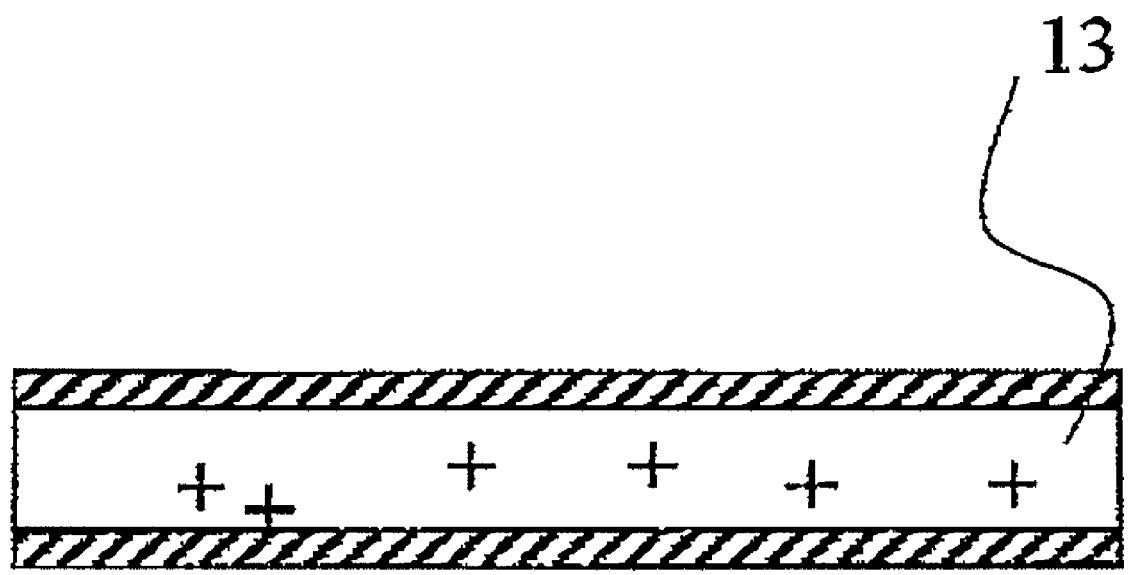
FIG. 3 is a diagram showing a charge accumulator of the silicon-based diaphragm electro-acoustic transducer according to the embodiment of the present invention.

FIG. 3 shows a concrete structure of the charge layer 8. In an example shown in FIG. 3, a silicon nitride $Si_3N_4$ layer 13 containing many defects is formed in the second silicon compound layer 5. In the case where a silicon nitride $Si_3N_4$ layer 13 containing many defects is used, compared with the case where a single float gate is used for a charge layer 8, the risk that the entire charge amount is lost in one leakage is smaller, however, it is disadvantageous in that it is difficult to emit charge with even distribution. This is not only because the charge is accumulated spatially at random, causing variation among transducers, but also because, since the cavity thicknesses of the center portion and end portion of the film are different from each other, the electric field intensities of the center portion and end portion are different from each other and charge is emitted only at the center portion of the film when a charge is emitted by the Fowler-Nordheim type tunnel current described below.

Figure 5:
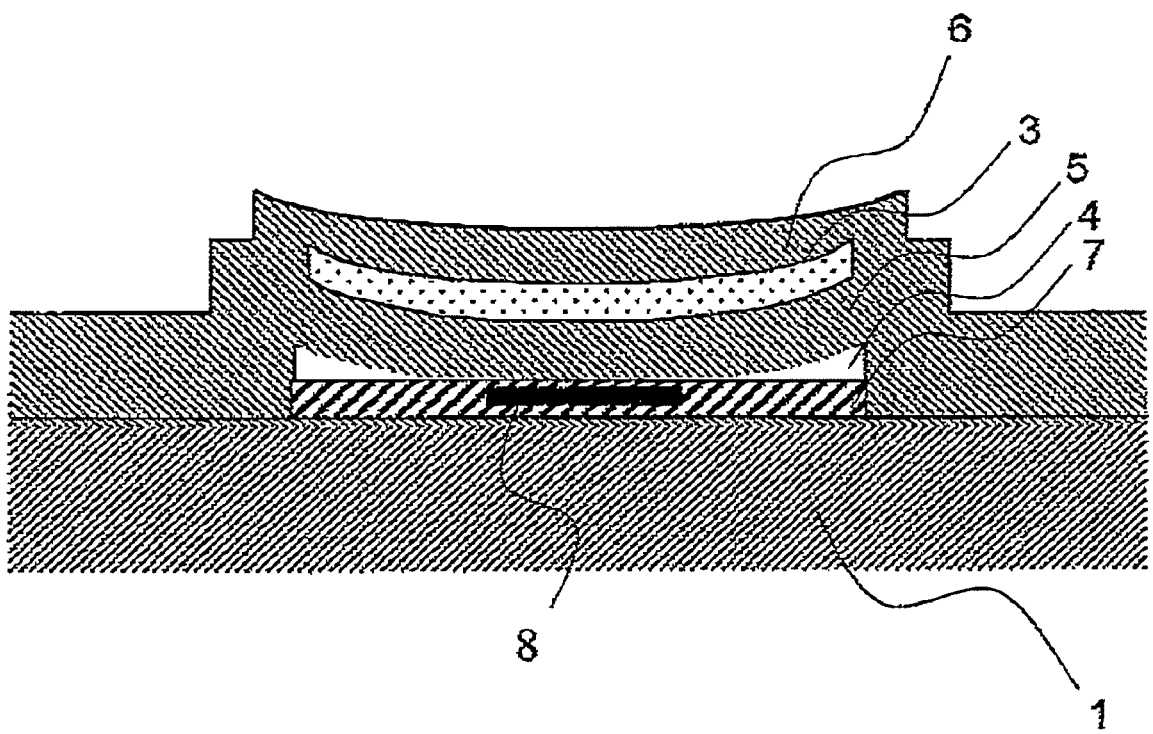
FIG. 5 is a cross sectional view of the charged silicon-based diaphragm electro-acoustic transducer, the view taken during charge emission according to the embodiment of the present invention.
Figure 6:
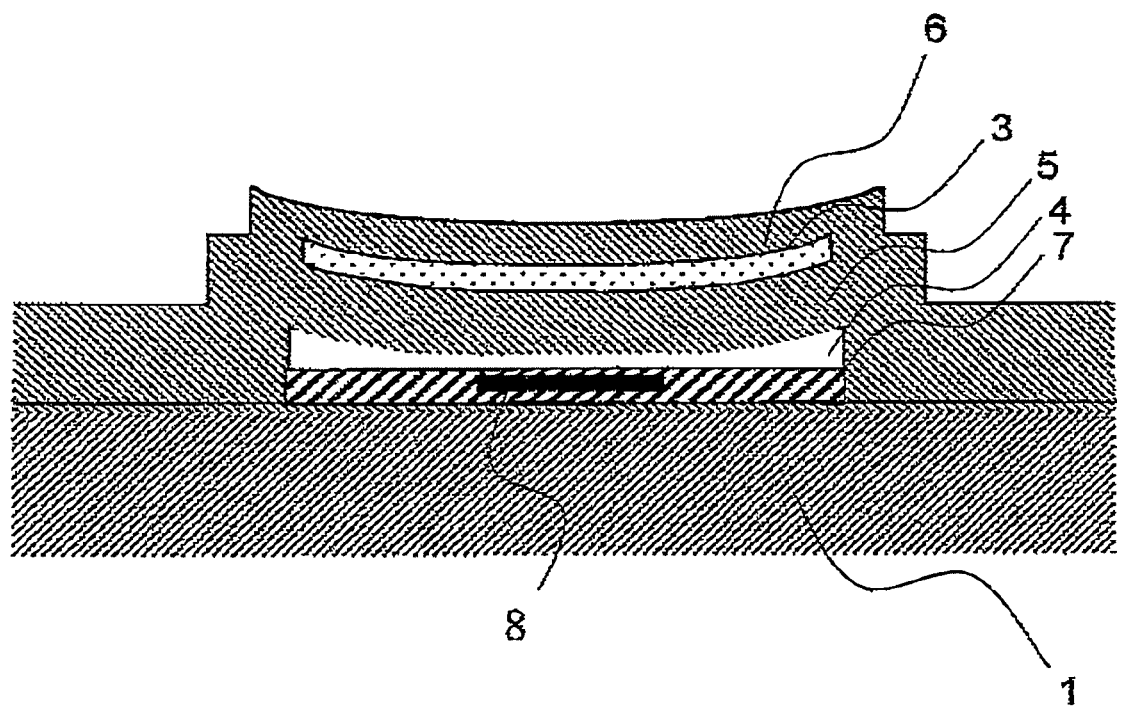
FIG. 6 is a cross sectional view of the silicon-based diaphragm electro-acoustic transducer according to the embodiment of the present invention, the view taken during when the transducer transmits/receives ultrasound.

Next, a method for emitting a charge will be described. Before voltage is applied between the top and bottom electrodes (between the top electrode 3 and the substrate 1 as the bottom electrode) shown in FIG. 4, when DC bias (approximately 100V) is applied, the center portion of the diaphragm is the most largely deformed, as shown in FIG. 5, and comes into contact with a surface of the second silicon compound layer 7 when the applied voltage exceeds a voltage called the collapse voltage. When voltage is further raised in this state, the length of the contact part increases with an increase in voltage. The distance between the top and bottom electrodes which was approximately 350 nm before the contact is reduced to 250 nm after the contact. Consequently, the electric field intensity becomes 1.4 times as large as the intensity before the contact. Thus, the electric field intensity between the charge layer 8 and the bottom electrode (substrate 1) increases in the contact part, a band structure of a tunnel barrier layer between the charge layer 8 and the bottom electrode is deformed, the Fowler-Nordheim (FN) type tunnel current flows, and charge is accumulated in the charge layer 8. When the DC bias is reduced in this state, the upper film is separated from the lower layer again as shown in FIG. 6, which has the effect of reduction in the voltage between the top and bottom electrodes and also the effect of an increase in the distance between the electrodes. Accordingly, the electric field intensity decreases and no FN tunnel occurs. Thus, the charge once locally present in the charge layer 8 can remain therein for a relatively long time. Thereafter, without applying a DC bias but by applying only AC pulses, the diaphragm oscillates by the amplitudes of the AC pulses and an amplitude proportional to an accumulated charge amount, and thus ultrasound can be transmitted. On the other hand, when an ultrasound is received from the outside, current flows between the top and bottom electrodes even if no DC bias is applied, the current being proportional to the change in the accumulated charge amount and a change in the capacitance by deformation of the diaphragm, and thus the transducer can be used as an ultrasound sensor. Although a method using hot electrons is applicable, in addition to the method using the FN tunnel, as a method for emitting a charge, a dedicated transistor is required to be incorporated.

Next, change in charge with elapsed time will be described. Since an ultrasound should be transmitted with an excellent ratio of signal to noise as much as possible, it is described above that an ultrasound transducer is used in a state shown in FIG. 6. However, actually in most cases, AC pulses are used with a high voltage where the voltage becomes close to the collapse voltage. In this case, the thickness of the cavity layer 4 becomes zero momentarily as shown in FIG. 5. In the case of a resonance frequency of 10 MHz, the contact time is approximately one tenth of one cycle period, that is, approximately 10 ns. Since the contact is repeated for each transmission of ultrasound, charge accumulated through a process reverse to a process for emitting charge returns to the top or bottom electrode.

Figure 7A:
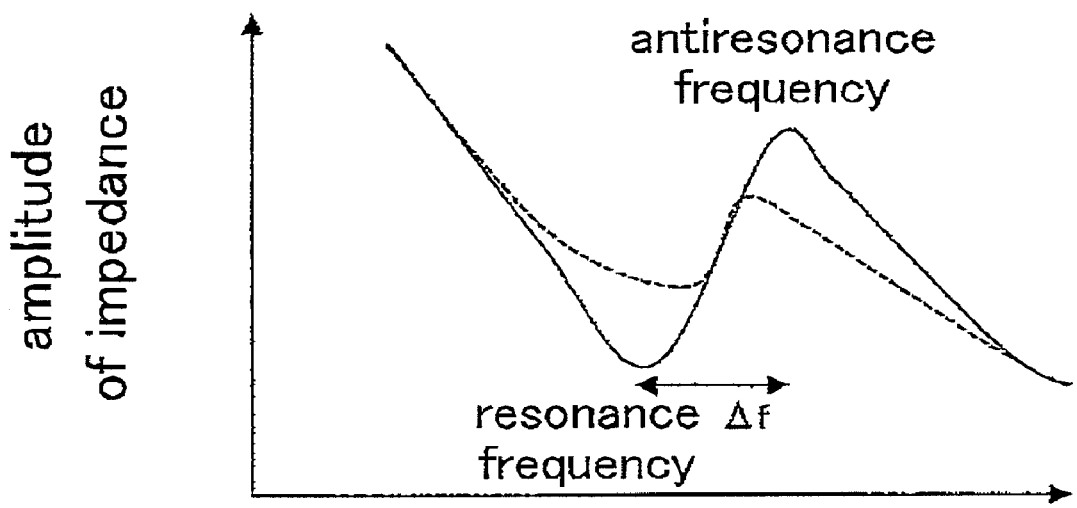
FIGS. 7A and 7B are diagrams showing the frequency spectrum of impedance of a diaphragm in another embodiment of the present invention.
Figure 7B:
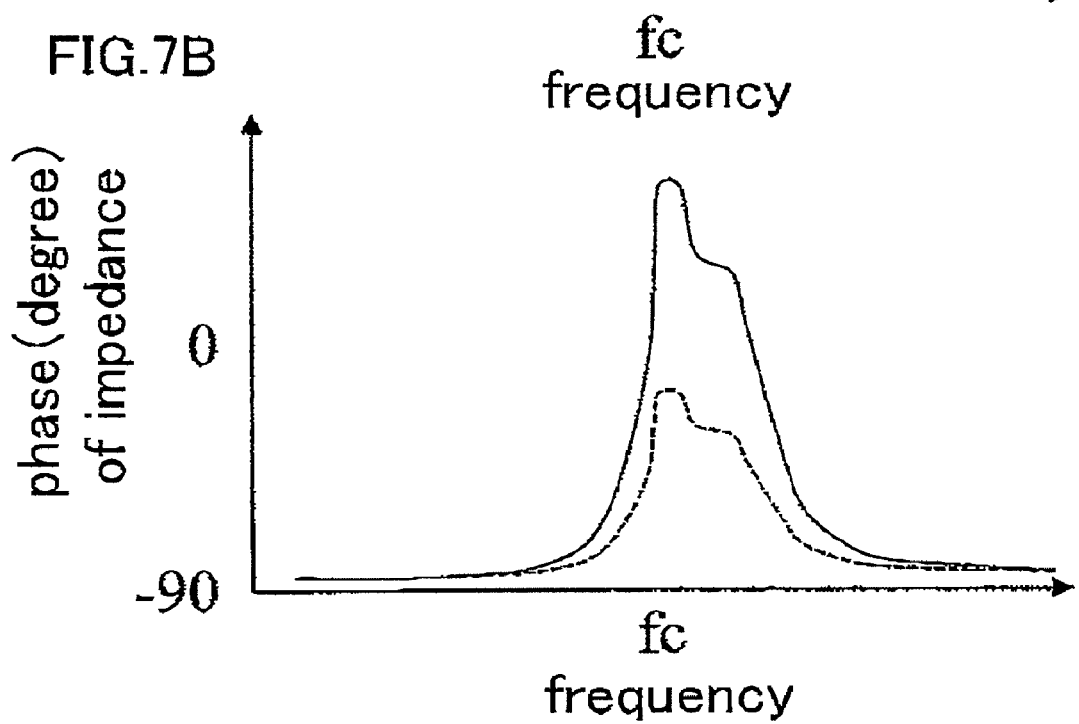

As a charge monitoring mechanism in the transducer, for example, a source electrode and drain electrode may be provided in the substrate. The resistance of an electron conductive channel between the source and a drain is proportional to the amount of charge accumulated in the charge layer 8. This is because the transducer has the same structure as a field effect transistor for which a charge layer 8 serves as a gate. Accordingly, periodic measurement of the resistance between the source and drain electrodes allows estimation of the charge amount remaining in the charge layer 8. This is because, since the transducer has the same structure as a field effect transistor in which a charge layer 8 serves as a gate, a current Isd between the source and drain is approximately proportional to gate voltage Vg, such as Isd∝Q (=Vg), wherein Q represents a charge amount accumulated in the charge layer 8. Therefore, the periodic measurement of the resistances between the source and drain electrodes allows estimation of the charge amount remaining in the charge layer 8. An embodiment, in which source and drain electrodes are arranged, will be described below with reference to FIG. 11. Corresponding to a change in charge amount, when the change is small, the change can be used for definition of a calibration coefficient and for calibration of a receive signal. When the change is large, the change can be used as a reference for determination on re-emitting. Although charge may be, of course, periodically and repeatedly emitted without monitoring, repetition of over-applying of current to an insulated layer serving as a tunnel path causes deterioration in the quality of the insulated layer. Therefore, re-emitting is desired to be reduced to the necessity minimum. A structure similar to that of the field effect transistor is described above as a monitoring method of the charge amount. However, another monitoring method, as shown in FIG. 7, is applicable that evaluates the frequency spectrum of impedance of a diaphragm. When electro-mechanical conversion efficiency of the diaphragm is large, the distance between the minimum point and the maximum point of amplitude of the impedance is increased. A difference Δf between frequencies at the minimum point and maximum point of the amplitude of the impedance is monitored so that the electro-mechanical conversion efficiency, that is, charge amount, of the diaphragm can be monitored. Further, monitoring can be performed by the use of a phase of the impedance. When the electro-mechanical conversion efficiency is high, that is, at a frequency close to a resonance frequency (fc), as the charge amount is large, the diaphragm acts as an inductance in terms of an electric circuit since a conversion rate from electrical energy to mechanical energy is high. At a frequency not close to the resonance frequency (fc), the diaphragm mostly acts as a capacitor since the conversion rate greatly drops. Thus, as indicated by a solid line in FIG. 7, a phase component of the impedance is −90° at a frequency not close to the resonance frequency (fc), and is 90° at a frequency close to the resonance frequency (fc). As the charge amount is reduced, the phase component is reduced from a peak of +90° as indicated by the dotted line in FIG. 7, and thus a change in the charge amount can be detected.

It is also possible to consider a method which makes a determination by monitoring a current between the top and bottom electrodes and using an integration value of the current. Any of the above-described methods enables an object of the present invention to be achieved.

In an ultrasonographic device, transmission/reception of ultrasound is not always carried out. For example, regarding a high frequency linear probe for observing a thyroid gland or carotid, a case of a depth of 10 cm, a visual range of 5 cm in a lateral direction, and a scan line density of 3 lines/mm in the lateral direction will be described. Since acoustic velocity in an organism is approximately 1500 m/s, it takes approximately 0.13 ms (=20 cm (a turn around distance per return)/ 1500 m/s) for a sound to travel to and return from a point at a depth of 10 cm. In order to obtain a single image, transmission/reception of sound wave is repeated 166 times (visual range width of 5 cm)/interval between scan lines of 0.3 mm) and thus one frame is produced. Consequently, it takes 22 ms to produce one frame. Even if it takes only a time of ms order to monitor the charge amount and re-emit charge for one transducer, it takes time required for approximately 10 frames, to perform this operation on each of approximately 200 transducers. Accordingly, monitoring each frame is impractical. It is possible to select a method of performing calibration for each patient, or a method of performing calibration even for one patient in a case of replacing the probe.

Figure 8:
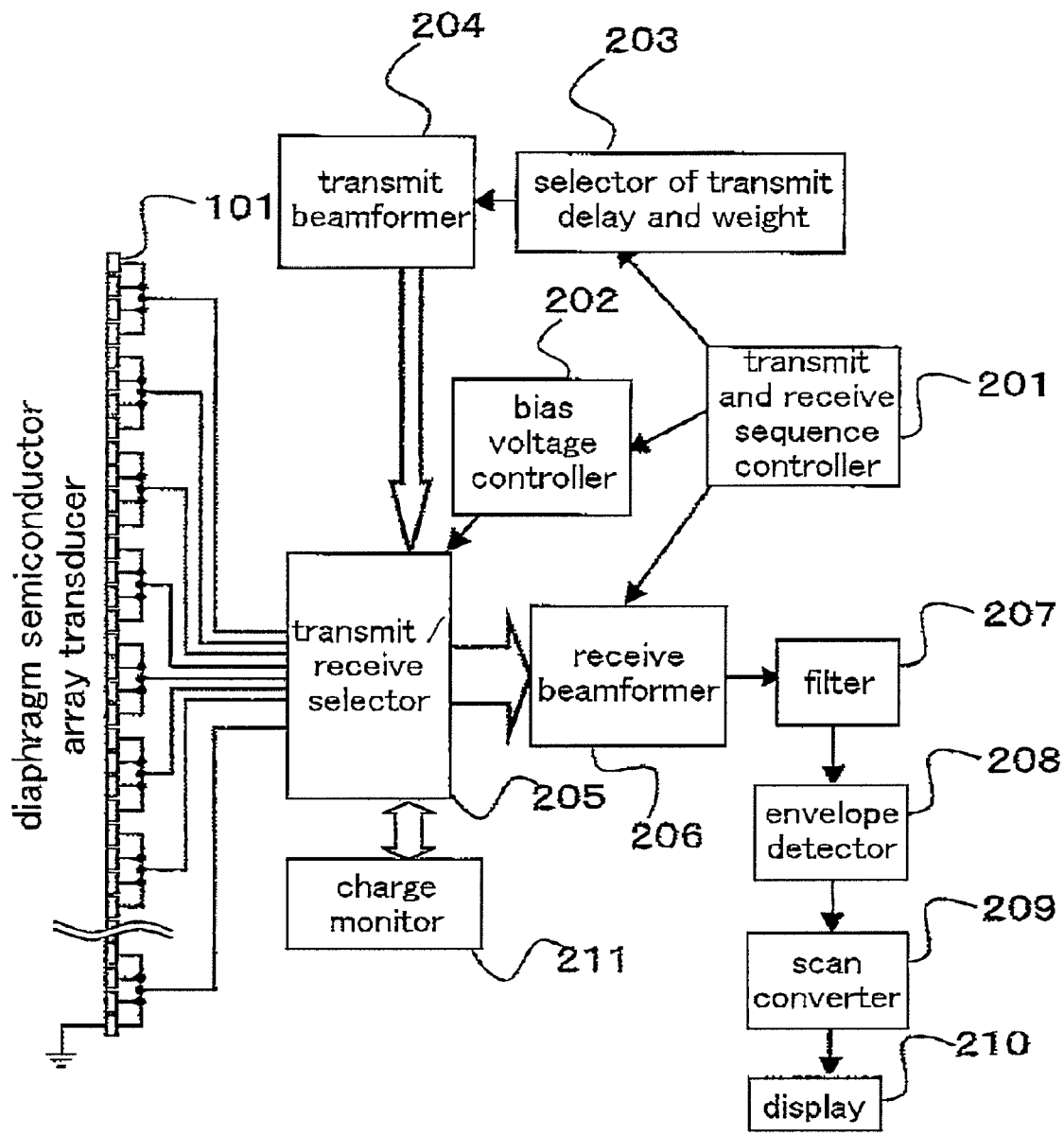
FIG. 8 is a block diagram of an ultrasonographic device including a charge monitor.
Figure 10:
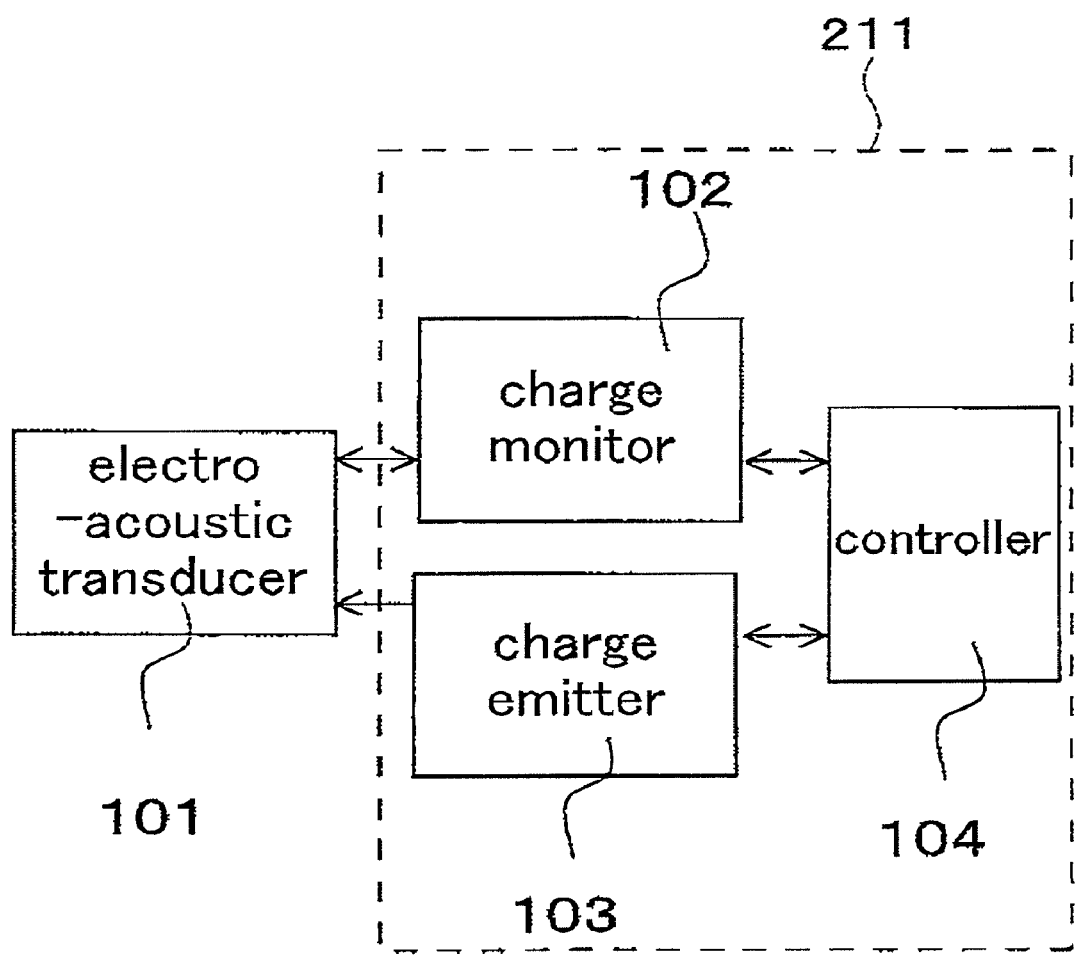
FIG. 10 is a block diagram of a charge monitor.

An ultrasonographic device according to the present invention will be described below with reference to FIG. 8, the device including the above described electro-acoustic transducers and a charge controller for controlling charge amounts accumulated in the electro-acoustic transducers. Based on control by a transmit and receive sequence controller 201 programmed in advance, in a selector of transmit delay and weight 203, values of transmit delay and weighting function for each channel are selected to be provided to a transmit beamformer 204. The transmit beamformer 204 provides a transmit pulse to an electro-acoustic transducer 101 based on these values via a transmit/receive selector 205. At this time, a bias voltage is also applied to the electro-acoustic transducer 101 by a bias voltage controller 202, and consequently, ultrasound is transmitted from the electro-acoustic transducer 101 to a subject (not shown). A part of the ultrasound reflected by a scatterer in the subject is received by the electro-acoustic transducer 101. The transmit and receive sequence controller 201 then controls a receive beamformer 206 to start a receive mode after a predetermined elapsed time from a timing of the transmission. The predetermined time is, for example, a sound turn around time per return for 1 mm in the case of obtaining an image at a depth deeper than 1 mm of the subject. The receive mode is not started immediately after transmission, because it is necessary to receive a voltage having an extremely small value generally in a range of one hundredth to one thousandth of the amplitude of a transmit voltage. The receive beamformer 206 continuously controls the delay and weighting function in accordance with an arrival time of the reflected ultrasound, the control being called dynamic focus. Data after the dynamic focus is converted into an image signal by an image former including a filter 207, an envelope detector 208, a scan converter 209 and the like, and then displayed on a display 210 as an ultrasound tomographic image. The present invention has a feature that the charge amount of the charge layer 8 in an electro-acoustic transducer 101 is monitored by a charge monitor 211 (charge controller). As described above, the charge amount is not required to be always monitored. It is preferable to carry out monitoring at the time of replacement of a probe, switching of a photographing mode even in the same probe, or the like, that is, at a timing of causing no trouble even in a charge monitoring and charge re-emitting process taking several 100 ms. As shown in FIG. 10, the charge monitor 211 has a charge monitoring section 102, a charge emitter 103 and a controller 104. Estimating from a phase change of impedance of each channel of the electro-acoustic transducers 101 of which change in the charge amount for each channel has been described above, when, for example, variation in the sensitivity of electro-acoustic transducers 101 is greater than 2 to 3 dB that is allowable as sensitivity variation in the transducers, charge is re-emitted by the charge emitter 103, the charge amount is re-monitored by the charge monitor 211, and this process can be repeated until it is confirmed that the sensitivity is within a desired sensitivity variation range.

Figure 11:
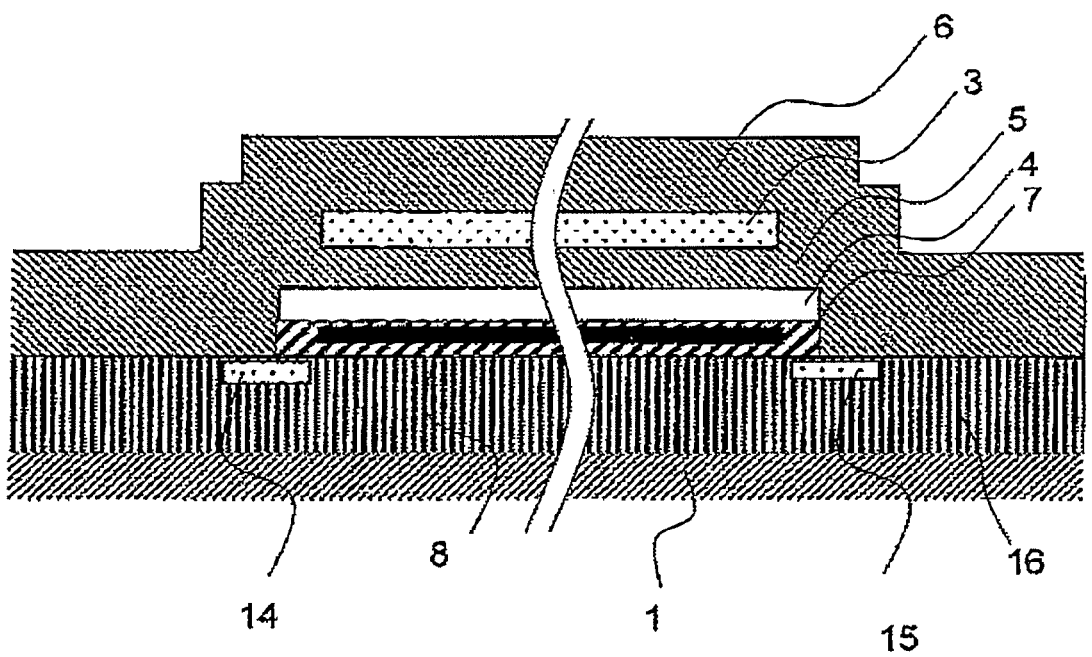
FIG. 11 is a cross sectional view of a silicon-based diaphragm electro-acoustic transducer according to another embodiment of the present invention.

Further, more precise monitoring can be performed by providing electrodes 14, 15 for the charge monitor as shown in FIG. 11. The precise monitoring can be realized by making the charge layer 8 correspond to a gate of a field effect transistor, and similarly making the electrodes for monitor 14, 15 correspond to the source and drain electrodes of the field effect transistor respectively. In a case of a field effect transistor, the resistance between the source and drain (between the electrodes 14 and 15) is determined based on the gate voltage. Likewise, the charge amount of the charge layer 8 can be measured by monitoring the resistance between electrodes 14 and 15 according to a constitution shown in FIG. 11. That is, in the present invention, as an example, an electro-acoustic transducer can be employed, the transducer having: a silicon-based or silicon compound-based substrate; a first electrode formed on or in the substrate; a silicon-based or silicon compound-based thin film formed on the substrate; a second electrode formed on or in the thin film; a cavity layer provided between the first and second electrodes; a charge layer for accumulating charges emitted from the first and second electrodes, the charge layer being provided between the first and second electrodes; and a source electrode and drain electrode for measuring a charge amount of the charge layer.

Figure 9:
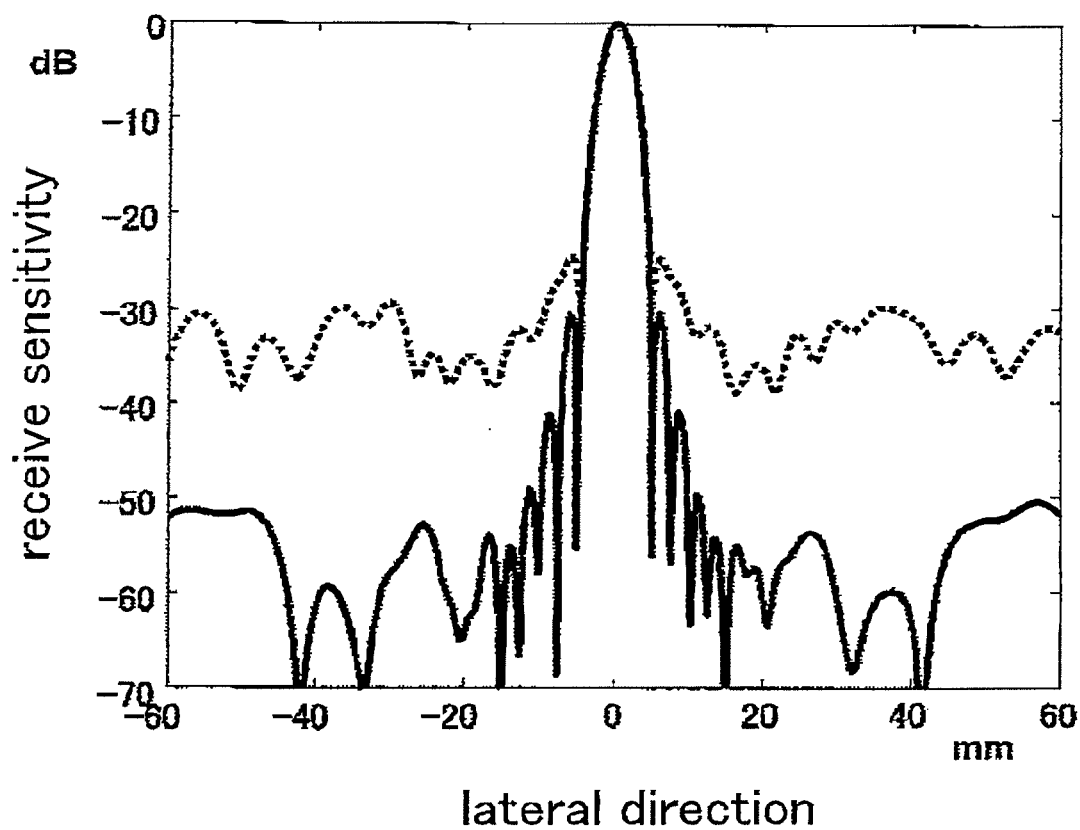
FIG. 9 is a graph indicating a calculation result of an ultrasound beam in an effect of the present invention.

An effect of the present invention will be described with reference to FIG. 9. FIG. 9 shows a beam pattern of an ultrasound, wherein the horizontal axis indicates a lateral direction, the vertical axis indicates receive sensitivity with a unit of dB, and the beam pattern is normalized by the maximum value of the sensitivity. Resolution in the lateral direction of an image is determined by sharpness of the center of the ultrasound beam, and it is first important that the main beam is sharp at 0 mm of the lateral direction. Further, since a dynamic range of the image is determined by a noise level at a part other than the center of the beam, the noise level at a part other than the center of the beam is also a significant evaluation factor. This is because, when the dynamic range of the image is small, all structures, each of which being positioned around scatterers with a large reflection brightness and having a small reflection brightness, are obscured by a noise level of the periphery of the scatterers having the large reflection brightness, and do not appear in the image. The solid line and dotted line in FIG. 9 indicate sensitivity variations of the transducers of 1 dB (solid line) and 6 dB (dotted line) respectively. That is, although an excellent beam pattern as indicated by the solid line in FIG. 9 is always obtained when the charge amount is monitored, a beam pattern as indicated by the dotted line in FIG. 9 is obtained and the dynamic range of the image is largely deteriorated when the change in the charge amount is not monitored.

The invention claimed is:

1. An ultrasonographic device comprising:
an ultrasound probe having a plurality of diaphragm electro-acoustic transducers for transmitting and receiving ultrasound, each electro-acoustic transducer having a charge layer;
an image former for forming an image from a signal received by the ultrasound probe;
a display for displaying the image;
a charge controller for controlling the charge amount of each charge layer;
wherein the charge controller comprises;
a charge monitor for monitoring the charge amount of each charge layer;
a charge emitter for emitting charge to each charge layer; and
a controller for controlling each charge amount to be emitted by the charge emitter, based on the corresponding charge amount monitored by the charge monitor.

2. The ultrasonographic device according to claim 1,
wherein each electro-acoustic transducer comprises a source electrode and a drain electrode; and
wherein the charge monitor monitors a charge amount of each charge layer by measuring a resistance between the source electrode and the drain electrode.

3. The ultrasonographic device according to claim 1, wherein the charge monitor monitors each charge amount by evaluating frequency spectrum of a phase component of impedance of the corresponding electro-acoustic transducer.

4. The ultrasonographic device according to claim 1, wherein the charge monitor monitors each charge amount by evaluating frequency spectrum of an amplitude component of impedance of the corresponding electro-acoustic transducer.

5. The ultrasonographic device according to claim 1,
wherein each electro-acoustic transducer comprises a top electrode and a bottom electrode, and
wherein the charge monitor monitors each charge amount by monitoring an integrated value of a current between the top and bottom electrodes.

6. The ultrasonographic device according to claim 1, wherein the controller controls the charge emitter so that difference between the charge amounts of the plurality of electro-acoustic transducers is within a predetermined range.

7. The ultrasonographic device according to claim 1, wherein the charge controller calibrates each receive sensitivity of the ultrasound probe, based on the charge amount of the corresponding charge layer.

8. The ultrasonographic device according to claim 1,
wherein the ultrasound probe comprises a top electrode, a bottom electrode and a silicon compound layer provided between the top and bottom electrodes, and
wherein the charge layer is provided in the silicon compound layer.

9. An ultrasonographic device comprising:
an ultrasound probe having a plurality of diaphragm electro-acoustic transducers, each electro-acoustic transducer having a charge layer;
a transmit and receive selector connected to the ultrasound probe;
a transmit beamformer for transmitting a transmit signal to the transmit and receive selector;
a bias voltage controller for controlling a bias voltage of each electro-acoustic transducer in the ultrasound probe via the transmit and receive selector;
a receive beamformer for processing a receive signal from the transmit and receive selector;
an envelope detector for processing a phasing signal from the receive beamformer;
a scan converter for outputting a video signal by a use of an output of the envelope detector;
a display for displaying an output of the scan converter as an image;

a charge controller for controlling a charge amount of each charge layer via the transmit and receive selector;
wherein the charge controller comprises:
a charge monitor for monitoring the charge amount of each charge layer;
a charge emitter for emitting charge to each charge layer; and
a controller for controlling each charge amount to be emitted by the charge emitter, based on the corresponding charge amount monitored by the charge monitor.

10. The ultrasonographic device according to claim 9, wherein each electro-acoustic transducer has a source electrode and a drain electrode, and
wherein the charge monitor monitors a charge amount of each charge layer by measuring a resistance between the source electrode and the drain electrode.

11. An ultrasonographic device according to claim 9, wherein the charge monitor monitors each charge amount by evaluating frequency spectrum of a phase component of impedance of the corresponding electro-acoustic transducer.

12. An ultrasonographic device according to claim 9, wherein the charge monitor monitors each charge amount by evaluating frequency spectrum of an amplitude component of impedance of the corresponding electro-acoustic transducer.

13. The ultrasonographic device according to claim 9, wherein
each electro-acoustic transducer comprises a top electrode and a bottom electrode, and
the charge monitor monitors each charge amount by monitoring an integrated value of a current between the top and bottom electrodes.

14. An ultrasonographic device according to claim 9, wherein the controller controls the charge emitter so that difference between the charge amounts of the plurality of electro-acoustic transducers is within a predetermined range.

15. The ultrasonographic device according to claim 9, wherein the charge controller calibrates each receive sensitivity of the ultrasound probe, based on the charge amount of the corresponding charge layer.

16. The ultrasonographic device according to claim 9,
wherein the ultrasound probe comprises a top electrode, a bottom electrode, and a silicon compound layer provided between the top and bottom electrodes, and
wherein the charge layer is provided in the silicon compound layer.

* * * * *